(12) United States Patent
Simeroth

(10) Patent No.: US 11,166,982 B2
(45) Date of Patent: Nov. 9, 2021

(54) MULTI-TYPE STEM CELL ACTIVATION WITH NANO SILVER

(71) Applicant: Harold H. Simeroth, Dana Point, CA (US)

(72) Inventor: Harold H. Simeroth, Dana Point, CA (US)

(*) Notice: Subject to any disclaimer, the term of this patent is extended or adjusted under 35 U.S.C. 154(b) by 284 days.

(21) Appl. No.: 16/588,894

(22) Filed: Sep. 30, 2019

(65) Prior Publication Data

US 2020/0108093 A1 Apr. 9, 2020

Related U.S. Application Data

(60) Provisional application No. 62/740,799, filed on Oct. 3, 2018.

(51) Int. Cl.
| | |
|---|---|
| *A61K 33/38* | (2006.01) |
| *A61K 8/9789* | (2017.01) |
| *A61K 9/00* | (2006.01) |
| *A61Q 19/08* | (2006.01) |
| *A61K 36/898* | (2006.01) |
| *A61K 36/30* | (2006.01) |
| *A61K 8/19* | (2006.01) |
| *A61K 36/51* | (2006.01) |
| *B82Y 5/00* | (2011.01) |

(52) U.S. Cl.
CPC ............ *A61K 33/38* (2013.01); *A61K 8/19* (2013.01); *A61K 8/9789* (2017.08); *A61K 9/0014* (2013.01); *A61K 36/30* (2013.01); *A61K 36/51* (2013.01); *A61K 36/898* (2013.01); *A61Q 19/08* (2013.01); *B82Y 5/00* (2013.01)

(58) Field of Classification Search
CPC .. A61K 2300/00; A61K 36/51; A61K 36/898; A61K 2800/413; A61K 2800/91; A61K 33/38; A61K 36/30; A61K 8/0241; A61K 8/19; A61K 8/9789; A61K 9/0014; A61K 9/0019; A61Q 19/08; B82Y 5/00
See application file for complete search history.

(56) References Cited

U.S. PATENT DOCUMENTS

| | | |
|---|---|---|
| 4,987,150 A | 1/1991 | Kurono |
| 7,250,181 B2 | 7/2007 | Ghosal |
| 8,709,506 B2 | 4/2014 | Shrivastava et al. |
| 9,732,071 B2 | 8/2017 | Patron et al. |
| 10,124,030 B2 | 11/2018 | Goldsberry et al. |
| 10,392,371 B2 | 8/2019 | Patron et al. |
| 2004/0156920 A1 | 8/2004 | Kane |
| 2013/0028995 A1 | 1/2013 | Shrivastava et al. |
| 2016/0150789 A1 | 6/2016 | Schafer Elejalde et al. |
| 2016/0374979 A1 | 12/2016 | Yamamoto et al. |
| 2016/0376263 A1 | 12/2016 | Patron et al. |
| 2017/0020796 A1 | 1/2017 | Bezivin |
| 2017/0087199 A1 | 3/2017 | Patron et al. |
| 2017/0143022 A1 | 4/2017 | Wicker et al. |
| 2017/0304371 A1 | 10/2017 | Goldsberry et al. |
| 2018/0015060 A1 | 1/2018 | Abreo et al. |
| 2018/0360792 A1 | 12/2018 | Yamamoto et al. |

*Primary Examiner* — Jeffrey T. Palenik
(74) *Attorney, Agent, or Firm* — Kirk A. Buhler; Buhler & Associates Patenting

(57) ABSTRACT

Compositions and methods are disclosed for facilitating dermal health, including compositions and methods specifically for reversing environmental and age-related damage to the skin, and for enhancing the healing of wounds in the skin. The composition may be a suspension for application proximal to an administration site in the skin, with the suspension comprising Swertia Chirata extract, Calanthe Discolor stein cell extract, *Symphytum officinale* stein cell extract, *Argania spinosa* callus culture extract, and silver nanoparticles. It may be seen that such a composition, and other contemplated compositions, may be operative, when applied as a suspension at the dermis in a therapeutically effective amount, to increase epidermal cell production, increase collagen and elastin production, and increase stein cell replication at the application site.

12 Claims, No Drawings

US 11,166,982 B2

MULTI-TYPE STEM CELL ACTIVATION WITH NANO SILVER

CROSS REFERENCE TO RELATED APPLICATION

This application claims the benefit of Provisional Application Ser. No. 62/740,799 filed Oct. 3, 2018 entitled "MULTI-TYPE STEM CELL ACTIVATION WITH NANO SILVER," the entire disclosure of which is hereby wholly incorporated by reference.

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATION-BY-REFERENCE OF MATERIAL SUBMITTED ON A COMPACT DISC

Not Applicable

BACKGROUND OF THE INVENTION

Field of the Invention

This invention relates to improvements in compositions and methods for facilitating dermal health, and more particularly to compositions and methods for actively recruiting skin stein cells for skin repair and rejuvenation.

Description of Related Art Including Information Disclosed Under 37 CFR 1.97 and 1.98

There exists great interest in the medical community in the potential application of therapies specifically involving stein cells as a clinical tool in improving dermal health. Today, at least three different types of stein cells have been identified as contributing to the process of skin repair and regeneration. These identified stein cells are epidermal stein cells (ESC), mesenchymal stein cells (MSC), and adipose stein cells (ASC).

Epidermal stein cells, which differentiate into the various daughter cells which form the epidermis, are understood to provide, among other things, the new epidermal growth needed for the day-to-day replacement of the outer layer Stratum Corneum barrier, as exfoliated keratin is lost to the environment.

Mesenchymal stein cells are multipotent stein cells found throughout the body which serve to provide the general tissue-repair function. In the dermis, mesenchymal stein cells migrate into the inter-follicular dermis around the dermal papilla where they proliferate and differentiate into fibroblast calls, which regenerate the extra-cellular matrix by producing new collagen and elastin—two components that are critical to maintaining skin elasticity, firmness, and strength.

Recently, research has also revealed that a tremendous number of adipose stein cells reside in the hypodermis, which is primarily a layer of fat that resides just under the dermal layer of the skin. It is now estimated that about 10% of the hypodermis tissue is composed of adipose stein cells, with the other 90% being lipid cells. When trauma occurs to the skin, the adipose stein cells are activated, whereupon they secrete growth factors and other cytokines that, among other things, provide signals which promote and modulate differentiation in epidermal stein cell and downregulate the inflammatory response.

In view of the fact that these different types of stein cells are all involved in the process of maintaining dermal health, it is important that therapies be developed which address the important roles played by each. However, existing therapies do not take this into consideration, instead only focusing on a providing more of, encouraging a differentiation in, or in upregulating activity of only a single type of stein cell. This ignores the critical fact that these stein cells and their recruitment and activation pathways are mutually reinforcing.

What is needed is compositions and methods which take into consideration recruitment and activation of multiple types of stein cells which play a role in dermal health.

BRIEF SUMMARY OF THE INVENTION

To solve these and other problems, compositions and methods for improving dermal health are contemplated. In an exemplary embodiment, it is contemplated that a composition would be formed as comprising an effective amount of Swerthia Chirata extract, Calanthe Discolor stein cell extract, *Symphytum officinale* stein cell extract, *Argania spinosa* callus culture extract, and silver nanoparticles. It may be seen that such a composition, and other contemplated compositions, may be operative, when applied as a suspension at the dermis in a therapeutically effective amount, to increase epidermal cell production, increase collagen and elastin production, and increase stein cell replication at the application site.

It is further contemplated that such suspensions may be formulated in a variety of ways for various types and routes of administration. For example, it is contemplated that the suspensions as presently disclosed may be formulated for topical administration at a dermal application site. Such formulations may include, without limitation, gels, creams, foams, lotions, and ointments.

It is also contemplated that the suspensions as presently disclosed may be formulated for application via injection proximal to a dermal application site. Such suspensions may be administered, for example, as a single injection proximal to the application site location, or via multiple injections at multiple locations, which may further be at various depths or locations in the dermis proximal to the application site.

Methods are additionally contemplated for using the herein discussed and contemplated suspensions for a variety of purposes. In particular, it may be seen that methods for mitigating and reversing environmental and age-related skin damage may be achieved via administering, at a an application site, a therapeutically effective amount of a suspension comprising Swertia Chirata extract, Calanthe Discolor stein cell extract, *Symphytum officinale* stein cell extract, *Argania spinosa* callus culture extract, and silver nanoparticles, wherein administration of the therapeutically effective amount of the suspension is operative to increase epidermal cell production, increase collagen and elastin production, and increase stein cell replication at the application site.

Likewise, it may be seen that methods for enhancing the healing of a wound may be achieved via administering, proximal to the wound, a therapeutically effective amount of a suspension comprising Swertia Chirata extract, Calanthe Discolor stein cell extract, *Symphytum officinale* stein cell extract, *Argania spinosa* callus culture extract, and silver nanoparticles, wherein administration of the therapeutically effective amount of the suspension is operative to increase epidermal cell production, increase collagen and elastin production, and increase stein cell replication at the application site.

Various objects, features, aspects, and advantages of the present invention will become more apparent from the following detailed description of preferred embodiments of the invention.

DETAILED DESCRIPTION OF THE INVENTION

It will be readily understood that the components of the present invention, as generally described and illustrated in the drawings herein, could be arranged and designed in a wide variety of different configurations. Thus, the following more detailed description of the embodiments of the system and method of the present invention, as represented in the drawings, is not intended to limit the scope of the invention, but is merely representative of various embodiments of the invention. The illustrated embodiments of the invention will be best understood by reference to the drawings, wherein like parts are designated by like numerals throughout.

According to an exemplary embodiment of the present disclosure, a Swerthia Chirata extract is contemplated as being a component of the suspension for improving dermal health. Swerthia Chirata, also called Indian gentian, Swerthia Chirayata, or Gentianaceae chirayata, is a plant indigenous to the temperate Himalayas that has been historically used in Ayurveda, Unani, and Siddha traditional medicines to purportedly treat a variety of ailments. Among other things, Swerthia Chirata extract is known to contain several bioactive phytoconstitutents, including amarogentin, ameroswerin, mangiferin, gentiopicrin, sweroside, swertiamarin, and swerchirin, among others.

Swerthia Chirata extract may be produced via extraction from the flowers, leaves, and/or stems of the Swerthia Chirata plant via known methods of producing extracts from herbs. In exemplary embodiments, the Swerthia Chirata extract is produced via an alcohol extraction process achieved by maceration of the plant and placement in ethanol or methanol, followed by filtration and subsequent evaporation of the alcohol component, leaving behind a thick gum extract, which may be readily reconstituted in a solvent such as a 10% DMSO solution. However, it may be seen that other known extraction processes may be utilized, as long a plurality of the above recited bioreactive phytoconstituents are extracted and are made available for subsequent incorporation into the suspension for improving dermal health.

In the exemplary embodiment, the Swerthia Chirata extract is included in the suspension for improving dermal health in an amount of 0.025% w/v. However, it may be seen that more or less Swerthia Chirata extract may be included, at that an inclusion of an amount of Swerthia Chirata extract in the suspension of as little as 0.0025% w/v may be sufficient to result in the desired synergistic therapeutic effect when applied in combination with a therapeutically effective amount of the other components of the suspension.

According to an exemplary embodiment of the present disclosure, Calanthe Discolor stein cell extract is contemplated as being a component of the suspension for improving dermal health. Calanthe Discolor is a species of orchid native to Japan. Importantly, Calanthe Discolor stein cell extract contains the indoles calanthoside and glucoindican. Calanthoside is an alkaloid which serves as a precursor glycoside in the plant to tryptanthrin, indierubin, and isatin. Both calanthoside and glucoindican have previously been observed to show an activating effect on blood flow when applied to the dermis. Calanthe Discolor stein cell extract also contain calaliukienoside, calaphenanthrenol, tryptanthrin, indierubin, isatin, and indican.

To obtain Calanth Discolor stein cell extract, meristematic (undifferentiated) cells are obtained from meristem regions of the Calanth Discolor plant, and those cells are subsequently lysed and homogenized via a lysis process, preferably a nonchemical process such as high-pressure homogenization. The lysate may then be stored in a glycerine:water medium prior to incorporation into the presently contemplated suspension.

In the exemplary embodiment, an amount of Calanth Discolor stein cell extract may be included in the suspension for improving dermal health in an amount such that the proportion of calanthoside in the final suspension is at a 0.5% w/v concentration and the proportion of glucoindican in the final suspension is at a 0.2% w/v concentration, alongside the other components of the Calanth Discolor stein cell extract. However, it may be seen that more or less Calanth Discolor stein cell extract may be included, and that an amount of Calanth Discolor stein cell extract included may result in a calanthoside concentration in the suspension of 0.1% w/v or less, and/or a glucoindican concentration in the suspension of 0.04% w/v or less may be sufficient to result in the desired synergistic therapeutic effect when applied in combination with a therapeutically effective amount of the other components of the suspension.

According to an exemplary embodiment of the present disclosure, *Symphytum officinale* stein cell extract is contemplated as being a component of the suspension for improving dermal health. *Symphytum officinale* is a species of flowering plant native to Europe that is also called comfrey, and its components have been used in many systems of traditional folk medicine, primarily for its analgesic, anti-inflammatory, antimicrobial, and antimycotic properties. Among other things, *Symphytum officinale* stein cell extract is known to contain several bioactive components, including allantoin, echimidine, symviridine, symphytine, intermedine, acetylintermedine, lycopsamine, lasiocarpine, and certain phenolic acids including rosmarinic, p-hydroxybenzoic, caffeic, chlorogenic, and p-coumaric acids.

To obtain *Symphytum officinale* stein cell extract, meristematic (undifferentiated) cells are obtained from meristem regions of the *Symphytum officinale* plant, and those cells are subsequently lysed and homogenized via a lysis process, preferably a nonchemical process such as high-pressure homogenization. The lysate may then be stored in a glycerine:water medium prior to incorporation into the presently contemplated suspension.

In the exemplary embodiment, an amount of *Symphytum officinale* stein cell extract may be included in the suspension for improving dermal health in an amount such that the concentration of allantoin in the final suspension is 0.6% to 2% w/v, alongside a proportionate amount of the other components of the *Symphytum officinale* stein cell extract. However, it may be seen that more or less *Symphytum officinale* stein cell extract may be included, and that an amount of *Symphytum officinale* stein cell extract included may result in a allantoin concentration in the suspension of 0.1% w/v or less, which may be sufficient to result in the desired synergistic therapeutic effect when applied in combination with a therapeutically effective amount of the other components of the suspension.

According to an exemplary embodiment of the present disclosure, *Argania spinosa* callus culture extract is contemplated as being a component of the suspension for improving dermal health. *Argania spinosa* is a rare and endangered species of tree, also called argan, that is only found in the protected semi-arid Sous basin in Morocco. Its primary economic product is argan oil, an oil that is produced from the kernels of the argan tree which has traditionally been used in Morocco for culinary and cosmetic purposes. Alongside its fatty acid constituents, argan oil is known to contain very high levels of γ-tocopherol as well as phenols such as caffeic acid, oleuropein, vanillic acid, tyrosol, catechol, resorcinol, (−)-epicatechin, and (+)-catechin. Typically, argan oil contains from 630 to 750 mg/kg of γ-tocopherol, which is four times higher than the level found in olive oil and twice that in hazelnut oil.

In plants, callus cells are cells which grow to cover a plant wound. Callus induction from somatic tissue is a known technique for generating plant tissue cultures which may proliferate via unlimited cell division. By triggering callogenesis from tissues of *Argania spinosa* via known techniques, an axigenic culture comprising a growing mass of unorganized *Argonia spinosa* parenchymal cells (the callus) may be established, similar in character to the meristem region of a normal plant. Due to the rarity and endangered status of the argan tree, callus induction and harvesting is preferred to direct harvesting of the meristem region of the argan tree itself. However, it may be seen that in alternative embodiments, direct harvesting of the meristem region of the argan tree may also result in production of an equivalent material to the callus culture extract of the presently contemplated exemplary embodiment.

To obtain *Argonia spinosa* callus culture extract, the cultured cells of the *Argonia spinosa* callus are lysed and homogenized via a lysis process, preferably a nonchemical process such as high-pressure homogenization. The lysate may then be stored in a glycerine/water medium prior to incorporation into the presently contemplated suspension.

According to an exemplary embodiment of the present disclosure, silver nanoparticles are contemplated as being a component of the suspension for improving dermal health. Silver nanoparticles, also called micronized silver or nano silver, are silver particles generally having a diameter of between 1 nm to 100 run. Silver nanoparticles have known utility as an antiseptic agent and a broad-spectrum antibiotic, causing cell death in certain bacterium via disruption of the cell membrane.

However, it has recently been discovered that silver nanoparticles may have a substantial effect upon stein cell activation, with the exact understanding of how this function is accomplished still being the subject of investigation. Specifically, in vivo silver nanoparticles may be seen to contribute to the activation of stein cells by increasing the active stein cell pool, both by the dedifferentiation of mature cells, and by the activation of more progenitor cells from existing stein cells.

Together, the five above discussed components contemplated for inclusion in the exemplary embodiment suspension of the present disclosure may be seen to combine and coordinate to recruit and activate each of the three different types of stein cells identified as contributing to the process of skin repair and regeneration—epidermal stein cells (ESC), mesenchymal stein cells (MSC), and adipose stein cells (ASC).

All three of these types of stein cells may be activated and, in the case of senescence, reactivated in the presence of the compositions of the present disclosure, both directly through the direct action of the constituents of the presently contemplated compositions upon the ESCs, and indirectly through downstream pathways triggered by the presence of the constituents of the presently contemplated composition. In particular, it is contemplated that the Swerthia Chirata extract will, among other things, directly stimulate the activity of the adipose stein cells in the hypodermis; the Calanthe Discolor stein cell extract will, among other things, directly stimulate the activity of the mesenchymal stein cells in the follicles and intrafollicular dermis; the *Symphytum officinale* stein cell extract will, among other things, directly stimulate the activity of the epidermal stein cells; the *Argania spinosa* callus culture extract will assist in protecting and vitalizing the dermal and hypodermal stein cells, and the silver nanoparticles will increase the available pool of stein cells to perform the herein described skin regenerative functions, as well as protecting the skin from potential microbial harm.

It has been found that the compositions as presently contemplated, instead of simply providing a summing effect of administering each component in isolation, actually have a multiplicative impact in the recruitment of stein cells involved in skin regeneration, which is thought to be due the effect of activating and recruiting the multiple interrelated groups of stein cells involved in skin regeneration, resulting in a positive feedback loop. Not only are the individuals types of stein cells each being directly activated, resulting in increased production of epidermal cells, collagen, elastin, and other components of the skin which are important for dermal health and regeneration, but more stein cells of each type are being recruited are created due to the activity of other components of the composition, as well as the downstream effects resulting from the activation of other types of stein cells. Together, this multiplicative effect results in a powerful composition for treating skin appearance damage and wound healing, and enhancing dermal health in general in a fashion that is rapid and highly effective.

The above description is given by way of example, and not limitation. Given the above disclosure, one skilled in the art could devise variations that are within the scope and spirit of the disclosure herein. Thus, specific embodiments of a multi-type cell activation with nano silver have been disclosed. It should be apparent, however, to those skilled in the art that many more modifications besides those described are possible without departing from the inventive concepts herein. The inventive subject matter, therefore, is not to be restricted except in the spirit of the appended claims.

The invention claimed is:

1. A method for mitigating and reversing environmental and age-related skin damage, the method comprising administering to a subject in need thereof, at an application site, a therapeutically effective amount of a suspension comprising:
   Swertia Chirata extract;
   Calanthe Discolor stein cell extract;
   *Symphytum officinale* stein cell extract;
   *Argania spinosa* callus culture extract, and
   silver nanoparticles;
   wherein administration of the therapeutically effective amount of the suspension is operative to increase epidermal cell production, increase collagen and elastin production, and increase stein cell replication at an application site.

2. The method to claim 1, wherein the suspension is formulated for topical application proximal to the application site.

3. The method to claim 2, wherein the suspension is formulated as a gel, a cream, a foam, a lotion, or an ointment.

4. The method to claim 1, wherein the suspension is formulated for application via injection proximal to the application site.

5. The method to claim 4, wherein the suspension is formulated for application via injection at a plurality of injection sites proximal to the application site.

6. The method to claim 1, wherein the silver nanoparticles have a diameter of between 1 nm to 100 nm.

7. A method for enhancing the healing of a wound, the method comprising administering to a subject in need thereof, proximal to the wound, a therapeutically effective amount of a suspension comprising:

Swertia Chirata extract;

Calanthe Discolor stein cell extract;

*Symphytum officinale* stein cell extract;

*Argania spinosa* callus culture extract, and silver nanoparticles;

wherein administration of the therapeutically effective amount of the suspension is operative to increase epidermal cell production, increase collagen and elastin production, and increase stein cell replication at an application site.

8. The method to claim 7, wherein the suspension is formulated for topical application proximal to the application site.

9. The method to claim 8, wherein the suspension is formulated as a gel, a cream, a foam, a lotion, or an ointment.

10. The method to claim 7, wherein the suspension is formulated for application via injection proximal to the application site.

11. The method to claim 10, wherein the suspension is formulated for application via injection at a plurality of injection sites proximal to the application site.

12. The method to claim 7, wherein the silver nanoparticles have a diameter of between 1 nm to 100 nm.

* * * * *